(12) United States Patent
Modi

(10) Patent No.: US 6,271,200 B1
(45) Date of Patent: Aug. 7, 2001

(54) PROTEINIC DRUG DELIVERY SYSTEM USING AEROSOLIZED MEMBRANE-MIMETIC AMPHIPHILES

(75) Inventor: Pankaj Modi, Ancaster (CA)

(73) Assignee: Generex Pharmaceuticals Inc., Toronto (CA)

( * ) Notice: Subject to any disclaimer, the term of this patent is extended or adjusted under 35 U.S.C. 154(b) by 0 days.

(21) Appl. No.: 09/397,701

(22) Filed: Sep. 16, 1999

Related U.S. Application Data

(60) Provisional application No. 60/113,242, filed on Dec. 21, 1998.

(51) Int. Cl.[7] .......................... A61K 38/28; A61K 38/00; A61K 51/00; A61K 9/00; A61K 9/66

(52) U.S. Cl. ........................... 514/4; 424/1.13; 424/400; 424/455; 514/2; 514/3; 514/8; 514/946; 514/950

(58) Field of Search .............................. 435/6, 455, 468, 435/458; 514/946, 950, 44, 2, 3, 4, 8; 424/1.13, 1.21, 1.29, 450, 455, 458, 400

(56) References Cited

U.S. PATENT DOCUMENTS

| | | |
|---|---|---|
| 4,614,730 | 9/1986 | Hansen et al. . |
| 4,708,861 | 11/1987 | Popescu et al. . |
| 4,772,471 | 9/1988 | Vanlerberghe et al. . |
| 4,830,857 | 5/1989 | Handjani et al. . |
| 4,839,111 | 6/1989 | Huang . |
| 4,900,730 | 2/1990 | Miyauchi . |
| 4,921,757 | 5/1990 | Wheatley et al. . |
| 5,004,611 | 4/1991 | Leigh . |
| 5,147,723 | 9/1992 | Wallach . |
| 5,230,884 | 7/1993 | Evans et al. . |
| 5,234,767 | 8/1993 | Wallach . |
| 5,260,065 | 11/1993 | Mathur et al. . |
| 5,292,499 | 3/1994 | Evans et al. . |
| 5,376,646 | 12/1994 | Pittrof et al. . |
| 5,514,670 | 5/1996 | Friedman et al. . |
| 5,591,713 | 1/1997 | Igari et al. . |
| 5,643,600 | 7/1997 | Mathur . |
| 5,653,987 | 8/1997 | Modi et al. . |
| 5,665,700 | 9/1997 | Cho et al. . |
| 5,690,954 | 11/1997 | Illum . |

FOREIGN PATENT DOCUMENTS

| | | |
|---|---|---|
| 0 200 383 | 12/1986 | (EP) . |
| 0 272 097 | 6/1988 | (EP) . |
| WO 96/40057 | 12/1996 | (WO) . |
| WO 97/42938 | 11/1997 | (WO) . |

OTHER PUBLICATIONS

Schofield, J. P. et al. Brit. Med. Bull., vol. 51, No. 1, pp. 56–71, 1995.*
Friedmann, T. Scientific American, Jun. Volume, pp. 96–101, 1997.*
Verma, I.M. et al. Nature, vol. 389, pp. 239–242, 1997.*
Crystal, R.G. Science, vol. 270, pp. 404–410, 1995.*
Branch, A.D. Trends in Biochem. Sci. (TIBS), vol. 23, pp. 45–50, 1998.*
Crooke, S.T. Antisense Research and Application. Chapter 1, pp. 1–50, 1998.*
Schreir, H. et al., Pulmonary Delivery of Liposomes, Journal of Controlled Release, 24(1993) pp. 209–223.

* cited by examiner

Primary Examiner—Andrew Wang
Assistant Examiner—Joe Zara
(74) Attorney, Agent, or Firm—Debra Z. Anderson; Eckert Seamans Cherin & Mellott, LLC

(57) ABSTRACT

A mixed liposome pharmaceutical composition with multilamellar vesicles is provided. The vesicles are comprised of a pharmaceutical agent, membrane-mimetic amphiphiles and various phospholipids. A method of making the composition using high speed mixing of the amphiphiles and phospholipids is also provided.

27 Claims, No Drawings

PROTEINIC DRUG DELIVERY SYSTEM USING AEROSOLIZED MEMBRANE-MIMETIC AMPHIPHILES

This is a continuation of Application No. 60/113242 filed Dec. 21, 1998.

FIELD OF THE INVENTION

The present invention relates to an improved delivery system for the administration of large-molecule pharmaceuticals, e.g. peptidic drugs, vaccines and hormones. In particular it relates to pharmaceuticals which may be administered through the oral and nasal membranes, or by pulmonary access.

BACKGROUND OF THE INVENTION

New methods of delivering large macromolecules (proteins and peptides) continue to be sought. One of the avenues investigated concerns the use of membrane-mimetic amphiphiles. A study of membrane-mimetic amphiphiles extends back to the first decade of the 20th century. Experiments using physical and chemical methods have shown that such molecules assume preferred arrays in the presence of water. Formation of these arrays, which includes micelles, monolayers and bimolecular layers is driven by the need of the polar head groups, which may be ionogenic or not, to associate with water, and the need of the polar hydrophobic tails to be excluded from water, (Small, D; Handbook of Lipid Research, vol. 4, 1986; Tanford, J: The Hydrophobic Effect, John Wiley & Sons, 1980; Fendler, J. Membrane Chemistry, 1982). Exactly which type of structure is assumed depends on upon the nature of the amphiphile, its concentration, the presence of other amphiphiles, temperature and the presence of salts and other solutes in the aqueous phase.

Membrane-mimetic amphiphiles include molecules that are insoluble in water but can take up water, and molecules that have appreciable solubility in water under limiting conditions. The former amphiphiles do not form molecularly disperse solutions in water but may swell considerably with water to form lamellar phases. The latter amphiphiles can, at some temperatures, form solutions of dispersed monomers in water and often undergo the following sequence as the concentration in water is increased: monomeric solution to micellar solution. The manufacture of non-phospholipid liposomes, depends on the manipulation of environmental variables (e.g. temperature, hydration and composition) in an appropriate temporal sequence so as to cause nonphospholipid amphiphiles to form liposomal structures.

Gebicki et al. (Nature, 243, 232, 1973: Chem. Phys. Lipids, 16, 142, 1976; Biochem. Biophys. Res. Commun. 80, 704, 1978; Biochemistry, 17, 3759, 1978) demonstrated the formation of water containing vesicles enclosed by oleic acid. Others, as disclosed for example in U.S. Pat. Nos. 4,772,471 and 4,830,857, and in J. Microencapsul. 4, 321, 1987, have made lipid vesicles from single tailed ether or esters derivatives of polyglycerol. These liposomes were found suitable for cosmetic products. Murakami et al (J. Am. Chem. Soc, 101, 4030, 1979; J. Am Oil Chem Soc. 66, 599, 1989) formed single compartment vesicles with one or more bilayer walls composed of cationic amphiphiles involving amino acid residues. Kaler et al (Science, 245, 1371, 1989) demonstrated that appropriate aqueous mixtures of single-tailed cationic and anionic surfactants spontaneously form single-walled vesicles, presumably via salt formation. Others have developed methods for manufacture of paucilamellar, non-phospholipid liposomes that can be formed from a variety of amphiphiles as well as from certain phospholipids. The liposomes have two or more membranes surrounding an amorphous core, each membrane being composed of amphiphile molecules in bilayer array. The core accounts for most of the vesicle volume and encapsulating substances.

The above-mentioned non-phospholipid based liposomes are mainly used for the delivery of moisturizers and cosmetic ingredients used topically or externally as creams or moisturizers. In some cases such liposomes may be used as an ointment for delivery of some pharmaceutical products. Many ingredients utilized in the above products have been found to be inadmissible in the human body and are not approved by the regulatory agencies around the world for the purpose of oral administration and as a vehicle for delivery of macromolecules (proteins and peptides) as life saving therapeutics. Furthermore, other non-phospholipid based liposomes have been developed for non-pharmaceutical applications, e.g. water-borne oil paints, surface cleansers, heavy duty industrial cleansers and skin-cleansing detergents.

Certain aspects of the present invention aims at the development of oral compositions consisting of mixture of certain non-phospholipid based membrane-mimetic amphiphiles (suitable and approved by the regulating agencies for oral formulation of human pharmaceutical products) in combination of specific phospholipids to form multilamellar liposomes which are very stable and are smaller than the pores of the gastrointestinal (GI) tract.

Relatively very little progress has been made in reaching the target of safe and effective oral formulations for peptides and proteins. The major barriers to developing oral formulations for proteins and peptides include poor intrinsic permeability, lumenal and cellular enzymatic degradation, rapid clearance, and chemical stability in the GI tract. Pharmaceutical approaches to address these barriers, which have been successful with traditional small, organic drug molecules, have not readily translated into effective peptide and protein formulations. Although the challenges are significant, the potential therapeutic benefits remain high especially in the field of diabetes treatment using insulin.

Researchers have explored various administration routes other than injection for proteins and peptides. These routes include administration through oral, intranasal, rectal, vaginal cavities for the effective delivery of large molecules. Out of the above four mentioned routes oral and nasal cavities have been of greatest interest. Both the oral and nasal membranes offer advantages over other routes of administration. For example, drugs administered through these membranes have a rapid onset of action, provide therapeutic plasma levels, avoid a first pass effect of hepatic metabolism, and avoid exposure of the drug to a hostile GI environment. Additional advantages include easy access to the membrane sites so that the drug can be applied, localized and removed easily. Further, there is a good potential for prolonged delivery of large molecules through these membranes.

The oral routes have received far more attention than have the other routes. The sublingual mucosa includes the membrane of ventral surface of the tongue and the floor of the mouth whereas the buccal mucosa constitutes the lining of the cheek. The sublingual mucosa is relatively permeable thus giving rapid absorption and acceptable bioavailability of many drugs. Further, the sublingual mucosa is convenient, acceptable and easily accessible. This route has been investigated clinically for the delivery of a substantial number of drugs.

Various mechanisms of action of penetration of large molecules using enhancers have been proposed.

These mechanisms of action, at least for protein and peptidic drugs include (1) reducing viscosity and/or elasticity of mucous layer, (2) facilitating transcellular transport by increasing the fluidity of the lipid bilayer of membranes, (3) facilitating paracellular transport by altering tight junction across the epithelial cell layer, (4) overcoming enzymatic barriers, and (5) increasing the thermodynamic activity of drugs (Critical Rev. 117–125, 1992).

Many penetration enhancers have been tested so far and some have been found effective in facilitating mucosal administration of large molecular drugs. However, hardly any penetration enhancing products have reached the market place. Reasons for this include lack of a satisfactory safety profile respecting irritation, lowering of the barrier function, and impairment of the mucocilliary clearance protective mechanism. It has been found that some of the popular penetration enhancers, especially those related to bile salts, and some protein solubilizing agents, impart an extremely bitter and unpleasant taste. This makes their use impossible for human consumption on a day to day basis. Several approaches were utilized to improve the taste of the bile salts based delivery systems, but none of them are commercially acceptable for human consumption to date. Approaches utilized include patches for buccal mucosa, bilayer tablets, controlled release tablets, liposome formulations, use of protease inhibitors, buccally administered film patch devices, and various polymer matrices. Further the problem is compounded because of the localized side effect of a patch which often results in severe tissue damage in the mouth.

The absorption of proteins and peptides is believed to be enhanced by the diffusion of large molecules entrapped in liposomal form through the aqueous pores and the cell structure perturbation of the tight paracellular junctions.

It has now been found that improvements in penetration and absorption of certain formulations can be achieved by mixing the formulation with propellants such as tetrafluoroethane, heptafluoroethane, dimethylfluoropropane, tetrafluoropropane, butane, isobutane, dimethyl ether and other non-CFC and CFC propellants, especially when delivered (e.g. applied to the buccal mucosa) through aerosol devices, e.g. metered dose inhalers (MDIs). Metered dose inhalers are a proven technology and a popular drug delivery form for many kinds of drug. The use of the present novel formulations and excipients can improve the quality (in terms of absorption), stability and performance of MDI formulations. The formulation ingredients are selected specifically to give enhancement in the penetration through the pores and facilitate the absorption of the drugs to reach therapeutic levels in the plasma. With the proper formulation changes and changes in administration technique, the formulation can be delivered to the deep lungs, through the nasal cavity and the buccal cavity.

Pressurized inhalers also offer a wide dosing range, consistent dosing efficiency. In this local delivery greater than 95% of the dose is reached to the target area. The smaller particle size (4–15 microns) of pressurized inhalers also enhances dosing due to broader coverage within the buccal cavity. In this situation, increased coverage can help more absorption of drug like insulin. Furthermore, because these devices are self-contained, the potential for contamination is avoided.

SUMMARY OF THE INVENTION

Accordingly the present invention provides an aerosol pharmaceutical formulation with multilamellar vesicles, comprising i) a pharmaceutical agent, ii) water, iii) an alkali metal C8 to C22 alkyl sulphate in a concentration of from 1 to 10 wt./wt. % of the total formulation, iv) at least one membrane-mimetic amphiphile, v) at least one phospholipid, vi) a phenol selected from the group consisting of phenol and methyl phenol in a concentration of from 1 to 10 wt./wt. % of the total formulation, and vi) a propellant selected from the group consisting of C1 to C2 dialkyl ether, butanes, fluorocarbon propellant, hydrogen-containing fluorocarbon propellant, chlorofluorocarbon propellant, hydrogen-containing chlorofluorocarbon propellant, and mixtures thereof, wherein the membrane-mimetic amphiphile is selected from the group consisting of lauramidopropyl betain, lauramide monoisopropanolamide, sodium cocoamphopropionate, bishydroxypropyl dihydroxypropyl stearammonium chloride, polyoxyethylene dihydroxypropyl stearammonium chloride, dioctadecyldimethylammonium chloride, sulphosuccinates, stearamide DEA, sodium tauro dihydro fusidate, fusidic acid, alkali metal isostearyl lactylates, alkaline earth metal isostearyl lactylates, panthenyl triacetate, cocamidopropyl phosphatidyl PG-diammonium chloride, stearamidopropyl phosphatidyl PG-diammonium chloride, borage amidopropyl phosphatidyl PG-diammonium chloride, borage amidopropyl phosphatidylcholine, polysiloxy pyrrolidone linoleyl phospholipid, octylphenoxypolythoxyethanol, and combinations thereof, and wherein the phospholipid is selected from the group consisting of, phospholipid GLA (glycolic, lactic acid), phosphatidyl serine, phosphatidylethanolamine, inositolphosphatides, dioleoylphosphatidylethanolamine, polysiloxy pyrrolidone linoleyl phospholipid, sphingomyelin, ceramides, cephalin, triolein, unsaturated lecithin, saturated lecithin and lysolecithin, and combinations thereof, and wherein the amount of each membrane-mimetic amphiphile and phospholipid is present in a concentration of from 1 to 10 wt./wt. % of the total formulation, and the total concentration of membrane-mimetic amphiphiles and phospholipids is less than 50 wt./wt. % of the formulation.

Preferably the mixed liposome pharmaceutical formulation has a pH of between 6.0 and 8.0.

The preferred number of membrane mimetic amphiphiles are from 2 to 5.

The preferred number of phospholipids are from 1 to 4.

In one embodiment, the alkali metal C8 to C22 alkyl sulphate is sodium C8 to C22 alkyl sulphate, and preferably is sodium lauryl sulphate.

Preferably, the ratio of proteinic pharmaceutical agent, e.g. insulin, to propellant is from 5:95 to 25:75.

In a further embodiment, the methyl phenol is m-cresol.

In another embodiment, the propellant is selected from the group consisting of tetrafluoroethane, tetrafluoropropane, dimethylfluoropropane, heptafluoropropane, dimethyl ether, n-butane and isobutane.

In yet another embodiment, the mixed liposome pharmaceutical formulation is contained in an aerosol dispenser.

In a preferred embodiment at least one protease inhibitor is added to the formulation to inhibit degradation of the pharmaceutical agent by the action of proteolytic enzymes. Of the known protease inhibitors, most are effective at concentrations of from 1 to 3 wt./wt. % of the formulation.

Non-limiting examples of effective protease inhibitors are bacitracin, soyabean trypsin, aprotinin and bacitracin derivatives, e.g. bacitracin methylene disalicylate. Bacitracin is the most effective of those named when used in concentrations of from 1.5 to 2 wt./wt. %. Soyabean trypsin and aprotinin may be used in concentrations of about 1 to 2 wt./wt. % of the formulation.

Preferably the lecithin is saturated lecithin.

It will be recognized by those skilled in the art that for many pharmaceutical compositions it is usual to add at least one antioxidant to prevent degradation and oxidation of the pharmaceutically active ingredients. It will also be understood by those skilled in the art that colorants, flavouring agents and non-therapeutic amounts of other compounds may be included in the formulation.

In one embodiment the antioxidant is selected from the group consisting of tocopherol, deteroxime mesylate, methyl paraben, ethyl paraben and ascorbic acid and mixtures thereof. A preferred antioxidant is tocopherol.

The pharmaceutical agent may be selected from a wide variety of macromolecular agents, depending on the disorder being treated, generally with molecular weights greater than about 1000 and especially between about 1000 and 2,000,000. Pharmaceutical agents useful in the present invention include insulin, heparin, low molecular weight heparin, hirugen, hirulos, hirudin, interferons, interleukins, cytokines, mono and polyclonal antibodies, chemotherapeutic agents, vaccines, glycoproteins, bacterial toxoids, growth hormones, parathyroid hormone (PTH), leutenizing hormones, oestrogens, androgens, calcitonins, insulin like growth factors (IGF), glucagon like peptides (GLP-1 and GLP-2), steroids and retinoids, injectable large molecule antibiotics, protein based thrombolytic compounds, platelet inhibitors, DNA, gene therapeutics, RNA and antisense oligonucleotides and small molecule drugs.

The present invention also provides a metered dose aerosol dispenser with the aerosol pharmaceutical formulation of the present invention therein.

The present invention also provides a method for administering an aerosol pharmaceutical formulations of the present invention, by spraying a predetermined amount of the formulation into the mouth with a metered dose spray device.

The present invention also provides a method for administration of a proteinic pharmaceutical agent in a buccal cavity of a human being by spraying into the cavity, without inhalation, from a metered dose spray dispenser, a predetermined amount of an aerosol pharmaceutical formulation with multilamellar vesicles, comprising i) a pharmaceutical agent, ii) water, iii) an alkali metal C8 to C22 alkyl sulphate in a concentration of from 1 to 10 wt./wt. % of the total formulation, iv) at least one membrane-mimetic amphiphile, v) at least one phospholipid, vi) a phenol selected from the group consisting of phenol and methyl phenol in a concentration of from 1 to 10 wt./wt. % of the total formulation, and vi) a propellant selected from the group consisting of C1 to C2 dialkyl ether, butanes, fluorocarbon propellant, hydrogen-containing fluorocarbon propellant, chlorofluorocarbon propellant, hydrogen-containing chlorofluorocarbon propellant, and mixtures thereof, wherein the membrane-mimetic amphiphile is selected from the group consisting of lauramidopropyl betain, lauramide monoisopropanolamide, sodium cocoamphopropionate, bishydroxypropyl dihydroxypropyl stearammonium chloride, polyoxyethylene dihydroxypropyl stearammonium chloride, dioctadecyldimethylammonium chloride, sulphosuccinates, stearamide DEA, sodium tauro dihydro fusidate, fusidic acid, alkali metal isostearyl lactylates, alkaline earth metal isostearyl lactylates, panthenyl triacetate, cocamidopropyl phosphatidyl PG-diammonium chloride, stearamidopropyl phosphatidyl PG-diammonium chloride, borage amidopropyl phosphatidyl PG-diammonium chloride, borage amidopropyl phosphatidylcholine, polysiloxy pyrrolidone linoleyl phospholipid, octylphenoxypolythoxyethanol, and combinations thereof, and wherein the phospholipid is selected from the group consisting of, phospholipid GLA (glycolic, lactic acid), phosphatidyl serine, phosphatidylethanolamine, inositolphosphatides, dioleoylphosphatidylethanolamine, polysiloxy pyrrolidone linoleyl phospholipid, sphingomyelin, ceramides, cephalin, triolein, unsaturated lecithin, saturated lecithin and lysolecithin, and combinations thereof, and wherein the amount of each membrane-mimetic amphiphile and phospholipid is present in a concentration of from 1 to 10 wt./wt. % of the total formulation, and the total concentration of membrane-mimetic amphiphiles and phospholipids is less than 50 wt./wt. % of the formulation.

DETAILED DESCRIPTION OF PREFERRED EMBODIMENTS

When developing new pharmaceutical formulations, it is desirable to provide dosage forms suitable for administering proteinic and peptidic drugs to humans and animals through oral, nasal, pulmonary and transdermal mucosal routes and to allow easy accessibility to the sites of administration. Local absorption of macromolecular drugs is desirable over a prolonged period to maximize drug absorption. Furthermore, it is desirable to minimize tissue damage and provide acceptable tissue compatibility of the dosage form. It is preferable to provide systems which are pain free and easy to be administered with great flexibility, in order to gain high acceptance and compliance of any therapy by patients.

It has been found that macromolecular drugs may be administered in liposomal formulations in which particle sizes (1 to 4 nm) are smaller than any pores of mucosal surfaces.

The present invention provides an improved method for delivery of macromolecular (high molecular weight) pharmaceutical agents, particularly through the skin or membranes in the nose, mouth or lungs. The preferred delivery is through oral or nasal cavities or through the lungs. The pharmaceutical agents cover a wide spectrum of agents, including proteins, peptides, hormones, vaccines and drugs. The molecular weights of the macromolecular pharmaceutical agents are preferably above 1000, especially between 1000 and 2,000,000.

For example, hormones which may be administered with the present invention include human growth hormones, parathyroid hormones, follicular stimulating hormones, luteinizing hormones, androgens, oestrogens, prostoglandins, somatropins, gonadotropins, erythropoetin, interferons, interleukins, steroids and cytokines.

Vaccines which may be administered with the present invention include bacterial and viral vaccines such as vaccines for hepatitis A, hepatitis B, hepatitis C, influenza, tuberculosis, canary pox, chicken pox, measles, mumps, rubella, pneumonia, BCG, HIV, helicobector pylori and AIDS.

Bacterial toxoids which may be administered using the present invention include diphtheria, tetanus, pseudonomas A and mycobactrium tuberculosis.

Examples of specific cardiovascular or thromobolytic agents include heparin, low molecular weight heparin, hirugen, hirulos and hirudin.

Small molecules may also be administered using the present invention. For example, opioids, narcotics, analgesics, NSAIDS, steroids, anaesthetics, hypnotics and pain killers, may be administered with the aerosol formulation of the present invention.

For insulin-containing and some other compositions, the composition may also contains at least one inorganic salt which opens channels in the gastrointestinal tract and may provide additional stimulation to release insulin. Non-limiting examples of inorganic salts are sodium, potassium, calcium and zinc salts, especially sodium chloride, potassium chloride, calcium chloride, zinc chloride and sodium bicarbonate.

It will be recognized by those skilled in the art that for many pharmaceutical compositions it is usual to add at least one antioxidant to prevent degradation and oxidation of the pharmaceutically active ingredients. It will also be understood by those skilled in the art that colorants, flavouring agents and non-therapeutic amounts of other compounds may be included in the formulation. Typically flavouring agents are menthol and other fruit flavors.

The antioxidant is selected from the group consisting of tocopherol, deteroxime mesylate, methyl paraben, ethyl paraben and ascorbic acid and mixtures thereof. A preferred antioxidant is tocopherol.

In a preferred embodiment at least one protease inhibitor is added to the formulation to inhibit degradation of the pharmaceutical agent by the action of proteolytic enzymes. Of the known protease inhibitors, most are effective at concentrations of from 1 to 3 wt./wt. % of the formulation.

Non-limiting examples of effective protease inhibitors are bacitracin, soyabean trypsin, aprotinin and bacitracin derivatives, e.g. bacitracin methylene disalicylate. Bacitracin is the most effective of those named when used in concentrations of from 1.5 to 2 wt./wt. %. Soyabean trypsin and aprotinin two may be used in concentrations of about 1 to 2 wt./wt. % of the formulation.

It is believed that the phenolic compounds act mainly as preservatives and complexing agents to stabilize drugs, e.g. insulin. Besides their function as a stabilizer and preservative, they may also act as antiseptic agents and furthermore may help in absorption. The methyl phenol may be o-cresol, m-cresol or p-cresol, but m-cresol is preferred.

As will be understood, the concentration of the pharmaceutical agent is an amount sufficient to be effective in treating or preventing a disorder or to regulate a physiological condition in an animal or human. The concentration or amount of pharmaceutical agent administered will depend on the parameters determined for the agent and the method of administration, e.g. nasal, buccal, pulmonary. For example, nasal formulations tend to require much lower concentrations of some ingredients in order to avoid irritation or burning of the nasal passages. It is sometimes desirable to dilute an oral formulation up to 10–100 times in order to provide a suitable nasal formulation.

Preferred methods of forming non-phospholipid membrane mimetic amphiphiles and phospholipid are based on the phase behaviour of lipid amphiphiles and phospholipids. Such methods use high turbulence or high shear methods of mixing, e.g. turbines or high velocity nozzles. For example, the membrane-mimetic amphiphiles may be injected at high velocity, e.g. through nozzles, into an aqueous phase of the phospholipid. Alternatively, the membrane mimetic amphiphiles and the phospholipids may be mixed in a mixing chamber into which the phospholipids are injected at high velocity through one or more nozzles and the membrane-mimetic amphiphiles are also injected at high velocity through one or more nozzles. Other ingredients, such as sodium lauryl sulphate, phenol and/or m-cresol, protease inhibitors may be premixed with either the membrane-mimetic amphiphile or the phospholipid. The velocity and mixing of the two liquids depends in part on the viscosities of the materials and nozzle diameters, e.g. to 15 m/s through 0.5 to 1.0 mm diameter nozzle apertures. Typically the ratio of the membrane-mimetic amphiphile aqueous solution to the phospholipid solution is about 5:1 to about 20:1 and the temperature of mixing is typically from about 10° C. to 20° C.

It may sometimes be necessary to heat the membrane-mimetic amphiphiles and other ingredients in order to yield a homogeneous aqueous solution prior to mixing with the phospholipids. The nature of the proteinic pharmaceutical may also dictate the temperature range at which mixing may take place. The temperature of mixing is typically room temperature or below, but may be higher than room temperature for certain formulations. The resulting formulation contains multi-lamellar liposomal vesicles. If the formulation has been heated during mixing, it is sometimes desirable to cool the mixture while still being mixed, in order to assist in the formation of the multi-lamellar vesicles.

Mixed multi-lamellar vesicles formed by the present process are very small in size, e.g. less than 10 nm, and are stable under most storage conditions.

Preferably, the membrane-mimetic amphiphile solution is injected into the phospholipid solution through tangentially placed nozzles in a small cylindrical mixing chamber. Preferably, one or two nozzles are used for the membrane-mimetic amphiphile solution and one or two alternating nozzles for the phospholipid solution. The two liquids are preferably delivered to the nozzles by flow-controlled positive displacement pumps.

The phenol and/or m-cresol are added to stabilize the formulation and protect against bacterial growth. An isotonic agent such as glycerin may also be added. The phenol and/or m-cresol and glycerin may be added after the membrane-mimetic amphiphile and phospholipids have been mixed, if desired, rather than with the other ingredients.

After formation of the pharmaceutical formulation, the formulation is charged to a pressurizable container. Preferably the container is a vial suitable for use with a metered dose dispenser, e.g. a metered dose inhaler or applicator. Then the vial is charged with propellant. As the propellant is introduced into the vial, there is great turbulence in the vial and the propellant and pharmaceutical formulation become mixed. Some of the formulations with glycerin or polyglycerin in them tend not to separate on standing. Others may separate. For those aerosol formulations which are substantially homogeneous, it may not be necessary to shake the vial before use, although, through habit with other formulations, many users may shake the vial. Shaking the vial is recommended, however, in order to assure good accuracy of pharmaceutical dispensing from "shot" to "shot" and from the first shot to the last from the container. As is known, in order to deliver the pharmaceutical agent to the lung, it is necessary for the user to breathe deeply when the aerosol spray from the pressurized container is released. Without breathing in, the pharmaceutical agent is delivered to the buccal cavity. The method chosen will depend on a number of factors, including the type of pharmaceutical agent, the concentration in the aerosol, the desired rate of absorption required and the like.

The preferred propellants are hydrogen-containing chlorofluorocarbons, hydrogen-containing fluorocarbons, dimethyl ether and diethyl ether. Even more preferred is HFC 134 a (1,1,1,2 tetrafluoroethane).

Although the present invention has such wide applicability, the invention is described hereinafter with particular reference to insulin and its analogues, which are used for the treatment of diabetes.

In the case of insulin, which is intended for administration through nasal or oral cavities or the lungs, an aqueous buffer solution may be made first by adding aqueous alkali metal C8 to C22 alkyl sulphate, e.g. sodium lauryl sulphate, to powdered insulin, and then stirring until the powder is dissolved and a clear solution is obtained. Typical concentrations of sodium lauryl sulphate in the aqueous solution are about 3 to 20 wt./wt. % in the solution. Typically, insulin is present in the solution in an amount which will give a concentration of about 2 to 4 wt./wt. % of the final formulation.

The buffer solution is then added to liquid which comprises a membrane-mimetic amphiphile or a phospholipid while mixing vigorously, to form multi-lamellar liposomal vesicles.

The membrane-mimetic amphiphile is selected from the group consisting of lauramidopropyl betain, lauramide monoisopropanolamide, sodium cocoamphopropionate, bishydroxypropyl dihydroxypropyl stearammonium chloride, polyoxyethylene dihydroxypropyl stearammonium chloride, dioctadecyldimethylammonium chloride, sulphosuccinates, stearamide DEA, sodium tauro dihydro fusidate, fusidic acid, alkali metal isostearyl lactylates, alkaline earth metal isostearyl lactylates, panthenyl triacetate, cocamidopropyl phosphatidyl PG-diammonium chloride, stearamidopropyl phosphatidyl PG-diammonium chloride, borage amidopropyl phosphatidyl PG-diammonium chloride, borage amidopropyl phosphatidylcholine, polysiloxy pyrrolidone linoleyl phospholipid, octylphenoxypolythoxyethanol, and combinations thereof.

The phospholipid is selected from the group consisting of phospholipid GLA, phosphatidyl serine, phosphatidylethanolamine, inositolphosphatides, dioleoylphosphatidylethanolamine, sphingomyelin, ceramides, cephalin, triolein, unsaturated lecithin, saturated lecithin and lysolecithin.

Each of the membrane-mimetic amphiphiles and phospholipids are present in a concentration of from 1 to 10 wt./wt. % of the total formulation.

The phenol and/or m-cresol may be added with the membrane mimetic amphiphile, the phospholipid or at any other time during mixing.

Other ingredients may be added to the liposomal solution. For example, flavouring agents, antioxidants, salts, protease inhibitors or other pharmaceutically acceptable compounds may be added.

In general the size of the multi-lamellar liposomal vesicle particles is about from 1 to 10 nm, and preferably from 1 to 5 nm. Such a size distribution ensures effective absorption of the formulation, and therefore the pharmaceutical agent, through the membranes, for example the membranes in the oral and nasal cavities.

The specific concentrations of the essential ingredients can be determined by relatively straightforward experimentation. For absorption through the nasal and oral cavities, it is often desirable to increase, e.g. double or triple, the dosage which is normally required through injection of administration through the gastrointestinal tract.

As will be understood, the amount of each component of the formulation will vary depending on the pharmaceutical agent and the site of application.

For oral application, sodium lauryl sulphate is insufficient on its own and must be combined with at least one membrane-mimetic amphiphile and at least one phospholipid to promote the oral absorption of macromolecules to achieve therapeutic effects. The effect is enhanced by delivery of the macromolecules by aerosol, with the additions of phenol and/or m-cresol to the formulation and using a propellant, particularly a hydrogen-containing fluorocarbon or a hydrogen-containing chlorofluorocarbon.

The oral aerosol formulations may be delivered with a suitable applicator.

Preferred formulations oral or nasal application have the following combinations, in addition to sodium lauryl sulphate:
  i) ceramide and stearamidopropyl phosphatidyl PG-diammonium chloride;
  ii) borage amidopropyl phosphatidyl PG-diammonium chloride and lecithin;

The therapeutic compositions of the present invention can be stored at room temperature or at cold temperature. Storage of proteinic drugs is preferable at a cold temperature, e.g. 4° C., to prevent degradation of the drugs and to extend their shelf life.

As indicated hereinbefore, generally, oral, pulmonary, transdermal and nasal are the favoured sites of the administration but the composition can be applied to the rectal and vaginal mucosa. According to the physiologically active peptide or protein used, the dosage form and the site of administration a specific administration method can be selected.

The composition of this invention is generally prepared as microfine multi-lamellar liposomal vesicle particles (1 to 10 nm or less) by the virtue of its preparation methods used and combinations suitable characteristics of the membrane mimetic amphiphiles and phospholipids.

Utilization of atomizer or aerosol spray devices (metered dose inhalers or nebulizers) can be used to further reduce the particle size for effective inhalation from the nasal or oral cavity so the drug may successfully reach to the specific site, especially the lungs, and be absorbed.

A particular advantage with the use of metered dose dispensers is that the formulation can be delivered in a relatively precise dose, e.g. titratable to injection within 1 unit of insulin dose. The droplet size of the formulation preferably falls between 1–5 $\mu$m in order for droplets to penetrate buccal mucosa or to reach to the deep lung surface. Thus, the present invention is suitable for delivery of proteinic drugs such as insulin for the treatment of diabetes.

The pressurized dispensers also offer a wide dosing range and consistent dosing efficiency. With such a delivery, greater than about 95% of the dose may reach the target area. The smaller particle size (1–5 $\mu$m) obtained using pressurized inhalers also enhances dosing due to broader coverage within the lung cavity. In this situation, increased coverage can help more absorption of a drug like insulin. Furthermore, because these devices are self-contained, potential contamination is avoided.

What is claimed is:
1. An aerosol pharmaceutical formulation with multilamellar vesicles, comprising i) a pharmaceutical agent, ii)

water, iii) an alkali metal C8 to C22 alkyl sulphate in a concentration of from 1 to 10 wt./wt. % of the total formulation, iv) at least one membrane-mimetic amphiphile, v) at least one phospholipid, vi) a phenol selected from the group consisting of phenol and methyl phenol in a concentration of from 1 to 10 wt./wt. % of the total formulation, and vii) a propellant selected from the group consisting of C1 to C2 dialkyl ether, butanes, fluorocarbon propellant, hydrogen-containing fluorocarbon propellant, chlorofluorocarbon propellant, hydrogen-containing chlorofluorocarbon propellant, and mixtures thereof, wherein the membrane-mimetic amphiphile is selected from the group consisting of lauramidopropyl betain, lauramide monoisopropanolamide, sodium cocoamphopropionate, bishydroxypropyl dihydroxypropyl stearammonium chloride, polyoxyethylene dihydroxypropyl stearammonium chloride, dioctadecyldimethylammonium chloride, hyaluronic acid, pharmaceutically acceptable salts of hyaluronic acid, sulphosuccinates, stearamide DEA, sodium tauro dihydro fusidate, fusidic acid, alkali metal isostearyl lactylates, alkaline earth metal isostearyl lactylates, panthenyl triacetate, cocamidopropyl phosphatidyl PG-diammonium chloride, stearamidopropyl phosphatidyl PG-diammonium chloride, borage amidopropyl phosphatidyl PG-diammonium chloride, borage amidopropyl phosphatidylcholine, polysiloxy pyrrolidone linoleyl phospholipid, octylphenoxypolythoxyethanol, and combinations thereof, and wherein the phospholipid is selected from the group consisting of, phospholipid GLA (glycolic, lactic acid), phosphatidyl serine, phosphatidylethanolamine, inositolphosphatides, dioleoylphosphatidylethanolamine, polysiloxy pyrrolidone linoleyl phospholipid, sphingomyelin, ceramides, cephalin, triolein, unsaturated lecithin, saturated lecithin and lysolecithin, and combinations thereof, and wherein each membrane-mimetic amphiphile and phospholipid is present in a concentration of from 1 to 10 wt./wt. % of the total formulation, and the total concentration of membrane-mimetic amphiphiles and phospholipids is less than 50 wt./wt. % of the formulation.

2. A formulation according to claim 1 wherein the alkali C8 to C22 metal alkyl sulphate is sodium lauryl sulphate.

3. A formulation according to claim 1 wherein there are at least two membrane mimetic amphiphiles.

4. A formulation according to claim 1 wherein the membrane-mimetic amphiphile is selected from the group consisting of hyaluronic acid, pharmaceutically acceptable salts of hyaluronic acid and mixtures thereof, the concentration being from about 1 to about 5 wt./wt. %.

5. A formulation according to claim 1 wherein said alkali metal C8 to C22 alkyl sulfate is sodium lauryl sulfate and said membrane-mimetic amphiphile and said phospholipid combination is selected from the group consisting of:

i) stearamidopropyl phosphatidyl PG-diammonium chloride and ceramide; and ii) borage amidopropyl phosphatidyl PG-diammonium chloride and lecithin.

6. A formulation according to claim 1 wherein the pharmaceutical agent is selected from the group consisting of insulin, heparin, low molecular weight heparin, hirugen, hirulos, hirudin, interferons, interleukins, cytokines, mono and polyclonal antibodies, chemotherapeutic agents, vaccines, glycoproteins, hormones, bacterial toxoids, growth hormones, calcitonins, insulin like growth factors (IGF), glucagon like peptides (GLP-1 or GLP-2), retinoids, injectable large molecule antibiotics, protein based thrombolytic compounds, platelet inhibitors, DNA, Gene therapeutics, RNA, antisense oligonucleotides, opioids, narcotics, analgesics, NSAIDS, steroids, anaesthetics, hypnotics and pain killers.

7. A formulation according to claim 6 wherein the pharmaceutical agent is insulin.

8. A process for making a pharmaceutical composition comprising:

mixing in a high shear mixer a pharmaceutical agent, water, an alkali metal lauryl sulphate in a concentration of from 1 to 10 wt./wt. % of the total formulation, at least one membrane-mimetic amphiphile and at least one phospholipid, wherein the membrane-mimetic amphiphile is selected from the group consisting of hyaluronic acid, pharmaceutically acceptable salts of hyaluronic acid, lauramidopropyl betain, lauramide monoisopropanolamide, sodium cocoamphopropionate, bishydroxypropyl dihydroxypropyl stearammonium chloride, polyoxyethylene dihydroxypropyl stearammonium chloride, dioctadecyldimethylammonium chloride, sulphosuccinates, stearamide DEA, gamma-linoleic acid, borage oil, evening of primrose oil, monoolein, sodium tauro dihydro fusidate, fusidic acid, alkali metal isostearyl lactylates, alkaline earth metal isostearyl lactylates, panthenyl triacetate, cocamidopropyl phosphatidyl PG-diammonium chloride, stearamidopropyl phosphatidyl PG-diammonium chloride, borage amidopropyl phosphatidyl PG-diammonium chloride, borage amidopropyl phosphatidylcholine, polysiloxy pyrrolidone linoleyl phospholipid, trihydroxy-oxo-cholanylglycine and alkali metal salts thereof, and octylphenoxypolythoxyethanol, polydecanol X-lauryl ether and polydecanol X-oleyl ether, wherein X is from 9 to 20, and wherein the phospholipid is selected from the group consisting of phospholipid GLA, phosphatidyl serine, phosphatidylethanolamine, inositolphosphatides, dioleoylphosphatidylethanolamine, sphingomyelin, ceramides, cephalin, triolein, lecithin, saturated lecithin and lysolecithin, and wherein each membrane mimetic amphiphile and phospholipid is present in a concentration of from 1 to 10 wt./wt. % of the total formulation, and the total concentration of membrane mimetic amphiphiles and phospholipids is less than 50 wt./wt. % of the formulation;

said mixing being continued until the composition is in multilamellar vesicle form; and adding a phenol selected from the group consisting of phenol, methyl phenol and mixtures thereof;

dispensing the resulting formulation into an aerosol container and charging the container with a propellant.

9. A process according to claim 8 wherein the membrane-mimetic amphiphile is selected from the group consisting of hyaluronic acid, pharmaceutically acceptable salts of hyaluronic acid and mixtures thereof, and the concentration of said membrane-mimetic amphiphile is from about 1 to 5 wt./wt. %.

10. A process according to claim 8 wherein the alkali metal lauryl sulphate is sodium lauryl sulphate.

11. A process according to claim 8 wherein the propellant is selected from the group consisting of hydrogen-containing chlorofluorocarbons, hydrogen-containing fluorocarbons, dimethyl ether and diethyl ether.

12. A process according to claim 8 wherein the pharmaceutical agent is selected from the group consisting of insulin, heparin, low molecular weight heparin, hirugen, hirulos, hirudin, interferons, interleukins, cytokines, mono and polyclonal antibodies, chemotherapeutic agents, vaccines, glycoproteins, hormones bacterial toxins, growth hormones, calcitonins, insulin like growth factors (IGF), glucagon like peptides (GLP-1 or GLP-2), retinoids, injectable large molecule antibiotics, protein based thrombolytic compounds, platelet inhibitors, DNA, RNA, gene therapeutics, antisense oligonucleotides, opioids, narcotics, analgesics, NSAIDS, steroids, anaesthetics, hypnotics and pain killers.

13. A process according to claim 8 wherein the pharmaceutical agent is insulin.

14. A process according to claim 8 wherein the method of mixing is a high turbulence or high shear method of mixing.

15. A process according to claim 14 selected from the group consisting of i) injecting the phospholipid, in liquid form, at high velocity through at least one nozzle into an aqueous phase of the membrane-mimetic amphiphile, ii) injecting the membrane-mimetic amphiphile, in liquid form, at high velocity through at least one nozzle into an aqueous phase of the phospholipid, and iii) injecting the phospholipid, in liquid form, at high velocity through at least one nozzle and the membrane mimetic amphiphile, in liquid form, at high velocity through at least one nozzle into a mixing chamber; and
  wherein the alkali metal lauryl sulphate is present with either the phospholipid or membrane-mimetic amphiphile.

16. A process according to claim 15 wherein the velocity of the phospholipid and amphiphile liquids is from 0 to 15 m/s through 0.5 to 1.0 mm diameter nozzle apertures.

17. A process according to claim 14 wherein the ratio of the membrane-mimetic amphiphile aqueous solution to the phospholipid solution is about 5:1 to about 20:1.

18. A process according to claim 15 wherein the ratio of the membrane-mimetic amphiphile aqueous solution to the phospholipid solution is about 5:1 to about 20:1.

19. A metered dose aerosol dispenser containing an aerosol pharmaceutical formulation with multilamellar vesicles, comprising i) a pharmaceutical agent, ii) water, iii) an alkali metal C8 to C22 alkyl sulphate in a concentration of from 1 to 10 wt./wt. % of the total formulation, iv) at least one membrane-mimetic amphiphile, v) at least one phospholipid, vi) a phenol selected from the group consisting of phenol and methyl phenol in a concentration of from 1 to 10 wt./wt. % of the total formulation, and vii) a propellant selected from the group consisting of C1 to C2 dialkyl ether, butanes, fluorocarbon propellant, hydrogen-containing fluorocarbon propellant, chlorofluorocarbon propellant, hydrogen-containing chlorofluorocarbon propellant, and mixtures thereof,
  wherein the membrane-mimetic amphiphile is selected from the group consisting of lauramidopropyl betain, lauramide monoisopropanolamide, sodium cocoamphopropionate, bishydroxypropyl dihydroxypropyl stearammonium chloride, polyoxyethylene dihydroxypropyl stearammonium chloride, dioctadecyldimethylammonium chloride, hyaluronic acid, pharmacologically acceptable salts of hyaluronic acid, sulphosuccinates, stearamide DEA, sodium tauro dihydro fusidate, fusidic acid, alkali metal isostearyl lactylates, alkaline earth metal isostearyl lactylates, panthenyl triacetate, cocamidopropyl phosphatidyl PG-diammonium chloride, stearamidopropyl phosphatidyl PG-diammonium chloride, borage amidopropyl phosphatidyl PG-diammonium chloride, borage amidopropyl phosphatidylcholine, polysiloxy pyrrolidone linoleyl phospholipid, octylphenoxypolythoxyethanol, and combinations thereof, and
  wherein the phospholipid is selected from the group consisting of, phospholipid GLA (glycolic, lactic acid), phosphatidyl serine, phosphatidylethanolamine, inositolphosphatides, dioleoylphosphatidylethanolamine, polysiloxy pyrrolidone linoleyl phospholipid, sphingomyelin, ceramides, cephalin, triolein, unsaturated lecithin, saturated lecithin and lysolecithin, and combinations thereof, and
  wherein each membrane-mimetic amphiphile and phospholipid is present in a concentration of from 1 to 10 wt./wt. % of the total formulation, and the total concentration of membrane-mimetic amphiphiles and phospholipids is less than 50 wt./wt. % of the formulation.

20. A metered dose aerosol dispenser according to claim 19 wherein the alkali metal C8 to C22 alkyl sulphate is sodium lauryl sulphate.

21. A metered dose aerosol dispenser according to claim 19 wherein there are at least two membrane mimetic amphiphiles.

22. A metered dose aerosol dispenser according to claim 19 wherein the membrane-mimetic amphiphile is selected from the group consisting of hyaluronic acid, pharmaceutically acceptable salts of hyaluronic acid and mixtures thereof, and the concentration of said membrane-mimetic amphiphile is from about 1 to 5 wt./wt. %.

23. A metered dose aerosol dispenser according to claim 19 wherein said alkali metal C8 to C22 alkyl sulfate is sodium lauryl sulphate and said membrane-mimetic amphiphile and said phospholipid combination is selected from the group consisting of:
  i) stearamidopropyl phosphatidyl PG-diammonium chloride and ceramide; and
  ii) borage amidopropyl phosphatidyl PG-diammonium chloride and lecithin.

24. A metered dose aerosol dispenser according to claim 19 wherein the pharmaceutical agent is selected from the group consisting of insulin, heparin, low molecular weight heparin, hirugen, hirulos, hirudin, interferons, interleukins, cytokines, mono and polyclonal antibodies, chemotherapeutic agents, vaccines, glycoproteins, hormones, bacterial toxoids, growth hormones, calcitonins, insulin like growth factors (IGF), glucagon like peptides (GLP-1 or GLP-2), steroids and retinoids, injectable large molecule antibiotics, protein based thrombolytic compounds, platelet inhibitors, DNA, Gene therapeutics, RNA, antisense oligonucleotides, opioids, narcotics, analgesics, NSAIDS, anaesthetics, hypnotics and pain killers.

25. A metered dose aerosol dispenser according to claim 19 wherein the pharmaceutical agent is insulin.

26. A method for administering an aerosol pharmaceutical formulation with multilamellar vesicles, comprising i) a pharmaceutical agent, ii) water, iii) an alkali metal C8 to C22 alkyl sulphate in a concentration of from 1 to 10 wt./wt. % of the total formulation, iv) at least one membrane-mimetic amphiphile, v) at least one phospholipid, vi) a phenol selected from the group consisting of phenol and methyl phenol in a concentration of from 1 to 10 wt./wt. % of the total formulation, and vii) a propellant selected from the group consisting of C1 to C2 dialkyl ether, butanes, fluorocarbon propellant, hydrogen-containing fluorocarbon propellant, chlorofluorocarbon propellant, hydrogen-containing chlorofluorocarbon propellant, and mixtures thereof, wherein the membrane-mimetic amphiphile is selected from the group consisting of lauramidopropyl betain, lauramide monoisopropanolamide, sodium cocamphopropionate, bishydroxypropyl dihydroxypropyl stearammonium chloride, polyoxyethylene dihydroxypropyl stearammonnium chloride, dioctadecyldimethylammonium chloride, hyaluronic acid, pharmaceutically acceptable salts of hyaluronic acid, sulphosuccinates, stearamide DEA, sodium tauro dihydro fusidate, fusidic acid, alkali metal isostearyl lactylates, alkaline earth metal isostearyl lactylates, panthenyl triacetate, cocamidopropyl phosphatidyl PG-diammonium chloride, stearamidopropyl phosphatidyl PG-diammonium chloride, borage amidopropyl phosphatidyl PG-diammonium chloride, borage amidopropyl phosphatidylcholine, polysiloxy pyrrolidone linoleyl phospholipid, octylphenoxypolythoxyethanol, and combinations thereof, and wherein the phospholipid is selected from the group consisting of phospholipid GLA (glycolic, lactic acid), phosphatidyl serine, phosphatidylethanolamine, inositolphosphatides, dioleoylphosphatidylethanolamine, polysiloxy pyrrolidone linoleyl phospholipid, sphingomyelin, ceramides, cephalin, triolein, unsaturated lecithin, saturated lecithin and lysolecithin, and combinations thereof, and wherein the amount of each membrane-mimetic amphiphile and phospholipid is present in a concentration of from 1 to 10 wt./wt. % of the total formulation, and the total concentration of membrane-mimetic amphiphiles and phospholipids is less than 50 wt./wt. % of the total formulation, by spraying a predetermined amount of the formulation into the buccal cavity without inhalation with a metered dose spray device, and wherein the pharmaceutical agent is selected from the group consisting of insulin, heparin, low molecular weight heparin, hirulog, hirugen, huridine, interferons, interleukins, cytokines, mono and polyclonal antibodies, immunoglobulins, proteinic vaccines, glycoproteins, hormones, calcitonins, insulin like growth factors (IGF), glucagon like peptides (GLP-1), large molecule antibiotics, protein based thrombolytic compounds, protein based platelet inhibitors, opioids, narcotics, hypnotics and steroids.

27. A method for administration of a pharmaceutical agent according to claim 26 wherein the pharmaceutical agent is insulin.

* * * * *

UNITED STATES PATENT AND TRADEMARK OFFICE
CERTIFICATE OF CORRECTION

PATENT NO.    : 6,271,200 B1
DATED         : August 7, 2001
INVENTOR(S)   : Modi Pankaj It is certified that error appears in the above-identified patent and that said Letters Patent is hereby corrected as shown below:

Title page,
Item [56], References Cited, U.S. PATENT DOCUMENTS add -- 5,733,572 3/1988 Unger et al --.

Column 8,
Line 10, after "e.g." add -- 10 --.

Column 13,
Line 8, add -- , -- after "hormones".
Lines 63 & 64, "pharmacologically" should read -- pharmaceutically --.

Column 14,
Line 55, insert -- steroids -- after "NSAIDS".

Column 15,
Line 4, "chliorofluorocarbon" should read -- chlorofluorocarbon --.

Signed and Sealed this

Sixth Day of August, 2002

*Attest:*

JAMES E. ROGAN
*Attesting Officer*   *Director of the United States Patent and Trademark Office*